(12) United States Patent
Otani et al.

(10) Patent No.: US 8,107,075 B2
(45) Date of Patent: Jan. 31, 2012

(54) OPTICAL CHARACTERISTIC MEASURING APPARATUS AND OPTICAL CHARACTERISTICS MEASURING METHOD

(75) Inventors: Yukitoshi Otani, Tokyo (JP); Toshitaka Wakayama, Saitama (JP)

(73) Assignee: Utsunomiya University, Utsunomiya-shi (JP)

( * ) Notice: Subject to any disclaimer, the term of this patent is extended or adjusted under 35 U.S.C. 154(b) by 619 days.

(21) Appl. No.: 11/887,410

(22) PCT Filed: Mar. 17, 2006

(86) PCT No.: PCT/JP2006/305342
§ 371 (c)(1),
(2), (4) Date: Feb. 20, 2009

(87) PCT Pub. No.: WO2006/103953
PCT Pub. Date: Oct. 5, 2006

(65) Prior Publication Data
US 2009/0213374 A1 Aug. 27, 2009

(30) Foreign Application Priority Data
Mar. 28, 2005 (JP) ................... 2005-092525

(51) Int. Cl.
*G01J 4/00* (2006.01)
(52) U.S. Cl. ........................ 356/364; 356/367
(58) Field of Classification Search .............. 356/364, 356/369, 326; 250/225, 559.09
See application file for complete search history.

(56) References Cited

U.S. PATENT DOCUMENTS

| 5,788,632 A | * | 8/1998 | Pezzaniti et al. | 600/316 |
| 7,420,675 B2 | * | 9/2008 | Giakos | 356/364 |
| 7,428,050 B2 | * | 9/2008 | Giakos | 356/369 |
| 2004/0114142 A1 | | 6/2004 | Wang | |

FOREIGN PATENT DOCUMENTS

| JP | 2002-543381 | 4/2000 |
| JP | 2003-172691 | 12/2001 |
| JP | 2004-530892 | 6/2002 |
| JP | 2005-241406 | 2/2004 |
| JP | 2005-257508 | 3/2004 |
| WO | WO 00/65331 | 4/2000 |
| WO | WO 02/103310 | 6/2002 |

OTHER PUBLICATIONS

U.S. Appl. No. 11/922,006, filed Feb. 6, 2008, Otani et al.
International Search Report for PCT/JP2006/305342 dated Jun. 6, 2006.

* cited by examiner

*Primary Examiner* — Layla Lauchman
(74) *Attorney, Agent, or Firm* — Posz Law Group, PLC

(57) ABSTRACT

An optical characteristic measuring apparatus includes an optical system 10 including first and second carrier retarders 24 and 32 having the retardations being known and differing from each other. The optical characteristic measuring apparatus performs: a spectrum extraction process of extracting a plurality of spectral peaks from a frequency spectrum obtained by analyzing a light intensity signal detected by light-receiving/spectroscopic means; and an optical characteristic element calculation process of calculating an optical characteristic element representing optical characteristics of a measurement target based on the spectral peaks and the retardations of the first and second carrier retarders.

10 Claims, 11 Drawing Sheets

AMPLITUDE DISTRIBUTION OBTAINED BY
FOURIER TRANSFORMATION

PHASE DISTRIBUTION OBTAINED BY
FOURIER TRANSFORMATION

ACTUAL EXPERIMENTAL RESULTS OF BIREFRINGENCE DISPERSION CHARACTERISTICS AND RINCIPAL AXIS DIRECTION OF REFERENCE RETARDATION PLATE

OPTICAL CHARACTERISTIC MEASURING APPARATUS AND OPTICAL CHARACTERISTICS MEASURING METHOD

TECHNICAL FIELD

The present invention relates to an optical characteristic measuring apparatus and an optical characteristic measuring method for measuring the optical characteristics of a measurement target.

BACKGROUND ART

In the field of research and development of polymer materials such as a liquid crystal, development of technology for measuring the optical characteristics (particularly the wavelength dependence of the retardation due to birefringence dispersion and the principal axis direction) of a measurement target has been demanded.

As measuring methods for the birefringence dispersion characteristics of a polymer material, technology of measuring the birefringence dispersion characteristics by means of a wavelength scan (see Patent Document 1), technology of simultaneously measuring the birefringence dispersion characteristics and the principal axis direction independent of a wavelength while rotating a wave plate and a polarizer (see Patent Document 2), technology enabling two-dimensional measurement of the birefringence dispersion characteristics in order to deal with a liquid crystal display production line (see Patent Document 3), and the like have been disclosed.

Patent Document 1: JP-A-2003-172691
Patent Document 2: JP-A-2005-241406
Patent Document 3: JP-A-2005-257508

DISCLOSURE OF THE INVENTION

However, when applying the related-art retardation measuring method to measurement of the wavelength dependence of the retardation, it is necessary to set the optical element and the phase shift of the measurement system in wavelength units. Therefore, it is difficult to measure the wavelength dependence of the retardation by one measurement within a short time.

According to the technologies disclosed in Patent Documents 1 and 3, it is necessary to separately calculate the retardation and the principal axis direction of the measurement target. Therefore, it is difficult to collectively calculate the retardation and the principal axis direction of the measurement target.

According to the technology disclosed in Patent Document 2, since the birefringence dispersion characteristics and the principal axis direction are measured while rotating part of the optical system, the birefringence within a predetermined wavelength region cannot be measured at the same time by causing measurement light to be incident on and exit from the measurement target only once (i.e., snap-shot measurement).

The invention has been achieved in view of the above-described problems. An objective of the invention is to provide an optical characteristic measuring apparatus and an optical characteristic measuring method capable of calculating the optical characteristic elements of the measurement target such as the principal axis direction and the retardation within a predetermined wavelength region by one measurement, and capable of measuring the principal axis direction of the measurement target and the retardation of the measurement target within a predetermined wavelength region by causing measurement light to be incident on and exit from the measurement target only once, as required.

(1) An optical characteristic measuring apparatus according to the invention in order to achieve the above object is an optical characteristic measuring apparatus for measuring optical characteristics of a measurement target, the optical characteristic measuring apparatus comprising:

an optical system including first and second carrier retarders having retardations being known and differing from each other, the optical system causing light including a predetermined band component to be incident on the measurement target through a first polarizer and the first carrier retarder and causing the light modulated by the measurement target to be incident on light-receiving/spectroscopic means through the second carrier retarder and a second polarizer; and calculation means for performing a spectrum extraction process of extracting a plurality of spectral peaks from a frequency spectrum obtained by analyzing a light intensity signal detected by the light-receiving/spectroscopic means, and an optical characteristic element calculation process of calculating an optical characteristic element representing the optical characteristics of the measurement target based on the spectral peaks and the retardations of the first and second carrier retarders.

According to the invention, the optical system including the first and second carrier retarders of which the retardations are known and differ from each other has a configuration in which light including a predetermined band component is modulated by the measurement target.

According to this configuration, when analyzing the light intensity signal of the measurement light detected by the light-receiving/spectroscopic means, the resulting frequency spectrum contains a plurality of spectral peaks reflecting the principal axis directions and the retardations of the first and second carrier retarders and the optical characteristics of the measurement target.

Therefore, when extracting the spectral peaks from the frequency spectrum, the spectral peaks can be expressed by a given theoretical equation including the optical characteristic element of the measurement target as a variable.

Since the retardations of the first and second carrier retarders are known in advance, the optical characteristic elements of the measurement target can be calculated by substituting the two spectral peaks and the retardations of the first and second carrier retarders in the theoretical equation.

According to the invention, since the optical characteristic elements of the measurement target can be calculated by one measurement of the measurement light including the predetermined band component (i.e., snap-shot measurement), the optical characteristics of the measurement target can be measured within a short time by using a simple configuration.

The term "optical characteristic element" used herein refers to various elements representing the optical characteristics of the measurement target. Examples of the optical characteristic element include the principal axis direction of the measurement target, the retardation, each matrix element of a matrix (e.g. Mueller matrix) representing the optical characteristics, dichroism, and the like. Specifically, the measuring apparatus according to the invention can measure one or more of these optical characteristic elements. The measuring apparatus according to the invention can measure the optical characteristics of the measurement target by calculating the optical characteristic elements.

In the invention, the optical characteristic measuring apparatus may be configured as a measuring apparatus (optical characteristic measuring apparatus) in which Fourier analysis is applied to the analysis process and which measures the principal axis direction and the retardation of the measurement target having optical transparency.

In this case, the measuring apparatus may be configured as a birefringence characteristic measuring apparatus which measures birefringence characteristics of a measurement target having optical transparency, the birefringence characteristic measuring apparatus comprising:

an optical system including first and second carrier retarders of which retardations are known and differ from each other, the optical system causing light including a predetermined band component to be incident on the measurement target through a first polarizer and the first carrier retarder and causing the light which has passed through the measurement target to be incident on light-receiving/spectroscopic means through the second carrier retarder and a second polarizer; and calculation means for performing a spectrum extraction process of extracting two spectral peaks from a Fourier spectrum obtained by subjecting a light intensity signal detected by the light-receiving/spectroscopic means to Fourier analysis, and a birefringence characteristic calculation process of calculating at least one of a principal axis direction of the measurement target and a retardation of the measurement target for the predetermined band component based on the two extracted spectral peaks and the retardations of the first and second carrier retarders.

(2) In the optical characteristic measuring apparatus of the invention, the calculation means may perform the spectrum extraction process before the optical characteristic element calculation process in a state in which the measurement target is not provided in the optical system, and calculate the retardations of the first and second carrier retarders as the known values based on the extracted spectral peaks.

According to the above configuration, even if the retardations of the first and second carrier retarders are unknown, the retardations of the first and second carrier retarders within a predetermined wavelength band can be calculated by performing the above snap-shot measurement in a state in which the measurement target is not provided in the optical system. Therefore, the optical characteristics of the measurement target can be measured by storing the calculated retardations of the first and second carrier retarders in a storage means of the calculation means as the known values.

(3) In the optical characteristic measuring apparatus of the invention, the optical system may be set so that:

a principal axis direction of the second polarizer is in a position rotated clockwise or counterclockwise by an odd-numbered multiple of 45 degrees with respect to a principal axis direction of the first polarizer;

a principal axis direction of the second carrier retarder is in a position rotated clockwise or counterclockwise by an odd-numbered multiple of 45 degrees with respect to a principal axis direction of the first carrier retarder; and the principal axis direction of the first carrier retarder is in a position rotated clockwise or counterclockwise by an odd-numbered multiple of 45 degrees with respect to the principal axis direction of the first polarizer.

According to the above configuration, the optical characteristics of the measurement target can be calculated by using a simple equation.

(4) In the optical characteristic measuring apparatus of the invention, the calculation means may calculate real number components and imaginary number components of the spectral peaks extracted by the spectrum extraction process, and may perform the optical characteristic element calculation process based on the real number components and the imaginary number components of the spectral peaks and the retardations of the first and second carrier retarders.

This enables the optical characteristic element of the measurement target to be simply calculated.

Specifically, the measuring apparatus may be configured as a device which measures the retardation and the principal axis direction of the measurement target utilizing Fourier analysis. In this case, the measuring apparatus may be configured to calculate a Fourier spectrum shown by the following equation $$F^{-1}[I(k)] = \tilde{I}(v) = \text{Bias} + C_{\alpha-\beta}(v) + C_{\alpha-\beta}^*(v) + C_{\alpha+\beta}(v) + C_{\alpha+\beta}^*(v) \quad (14)$$

by subjecting the light intensity signal I(k) detected by the light-receiving/spectroscopic means to Fourier analysis with respect to the wave number k, and extract two spectral peaks $C_{\alpha-\beta}(v)$ and $C_{\alpha+\beta}(v)$ from the Fourier spectrum in the spectrum extraction process, and in the birefringence characteristic calculation process, subject the two spectral peaks $C_{\alpha-\beta}(v)$ and $C_{\alpha+\beta}(v)$ to Fourier analysis based on the following equation $$F[C_{\alpha-\beta}(v)] = c_{\alpha-\beta}(k)$$

$$F[C_{\alpha+\beta}(v)] = c_{\alpha+\beta}(k) \quad (15\text{-}1)$$

and calculate the retardation $\Delta(k)$ and the principal axis direction $\theta$ of the measurement target based on the following equation $$\Delta(k) = \tan^{-1} \frac{\sqrt{m_{23}(k)^2 + m_{31}(k)^2}}{m_{33}(k)} \quad (18)$$

$$= \tan^{-1} \frac{\sqrt{\left(\frac{b_{\alpha+\beta}(k)-}{b_{\alpha-\beta}(k)}\right)^2 + \left(\frac{b_{\alpha-\beta}(k)+}{b_{\alpha+\beta}(k)}\right)^2}}{a_{\alpha-\beta}(k) - a_{\alpha+\beta}(k)}$$

$$\theta = \frac{1}{2}\tan^{-1} \frac{m_{31}(k)}{m_{23}(k)}$$

$$= \frac{1}{2}\tan^{-1} \frac{b_{\alpha-\beta}(k) + b_{\alpha+\beta}(k)}{b_{\alpha+\beta}(k) - b_{\alpha-\beta}(k)}$$

by utilizing the fact that $\text{amp}_{\alpha-\beta}$, $\phi_{\alpha-\beta}$, $\text{amp}_{\alpha+\beta}$, and $\phi_{\alpha+\beta}$ can be expressed as follows $$\text{amp}_{\alpha-\beta}(k) = \sqrt{\text{Re}[c_{\alpha-\beta}(k)]^2 + \text{Im}[c_{\alpha-\beta}(k)]^2}, \quad (16)$$

$$(\alpha - \beta)\delta(k) - \phi_{\alpha-\beta}(k) = \tan^{-1} \frac{\text{Im}[c_{\alpha-\beta}(k)]}{\text{Re}[c_{\alpha-\beta}(k)]}$$

$$\text{amp}_{\alpha+\beta}(k) = \sqrt{\text{Re}[c_{\alpha+\beta}(k)]^2 + \text{Im}[c_{\alpha+\beta}(k)]^2},$$

$$(\alpha + \beta)\delta(k) - \phi_{\alpha+\beta}(k) = \tan^{-1} \frac{\text{Im}[c_{\alpha+\beta}(k)]}{\text{Re}[c_{\alpha+\beta}(k)]}$$

based on the real number component Re and the imaginary number component Im of each spectral peak and the retardations of the first and second carrier retarders, and that $a_{\alpha-\beta}(k)$, $a_{\alpha+\beta}(k)$, $b_{\alpha-\beta}(k)$, and $b_{\alpha+\beta}(k)$ can be expressed as follows by using above-described $\text{amp}_{\alpha-\beta}(k)$, $\phi_{\alpha-\beta}(k)$, $\text{amp}_{\alpha+\beta}(k)$, and $\phi_{\alpha+\beta}(k)$.

$$a_{\alpha-\beta}(k) = \text{amp}_{\alpha-\beta}(k) \cdot \cos \phi_{\alpha-\beta}(k), \, a_{\alpha+\beta}(k) = \text{amp}_{\alpha+\beta}(k) \cdot \cos \phi_{\alpha+\beta}(k),$$

$$b_{\alpha-\beta}(k) = \text{amp}_{\alpha-\beta}(k) \cdot \sin \phi_{\alpha-\beta}(k), \, b_{\alpha+\beta}(k) = \text{amp}_{\alpha+\beta}(k) \cdot \sin \phi_{\alpha+\beta}(k) \quad (17)$$

This enables the retardation and the principal axis direction to be simply calculated.

(5) In the optical characteristic measuring apparatus of the invention, when the retardations of the first and second carrier retarders are $\alpha\delta$ and $\beta\delta$, the retardations of the first and second carrier retarders may be set so that a ratio of $(\alpha+\beta)$ to $(\alpha-\beta)$ is two or more or ½ or less.

This enables the difference in frequency between the spectral peaks to be sufficiently increased. Therefore, the optical characteristics of the measurement target can be measured more accurately.

(6) In the optical characteristic measuring apparatus of the invention, the light-receiving/spectroscopic means may include a plurality of light-receiving sections arranged two-dimensionally;

the optical system may be configured so that the light including the predetermined band component is incident on a predetermined region of the measurement target and the light modulated by the measurement target is incident on the light-receiving sections; and the calculation means may perform the spectrum extraction process and the optical characteristic element calculation process in units of the light-receiving sections to calculate the optical characteristic element in the predetermined region of the measurement target.

The retardation in a predetermined region of the measurement target can be easily measured by snap-shot measurement by causing the measurement light (i.e., light which has passed through the measurement target) to be incident on the two-dimensionally arranged light-receiving sections of the light-receiving/spectroscopic means, and performing the spectrum extraction process and the optical characteristic element calculation process in units of the light-receiving sections.

According to the invention, when causing light with a predetermined stretch to pass through regions of the measurement target with a predetermined width or area, the optical characteristic element calculation process for these region can be performed at the same time.

In other words, the invention enables the optical characteristics of the measurement target in predetermined regions (regions with a predetermined width or area) with a predetermined stretch to be measured at the same time by performing the spectrum extraction process and the optical characteristic element calculation process in units of the light-receiving sections.

In the invention, each light-receiving section may be configured to be able to acquire the intensity of incident light in frequency band units. For example, the light-receiving section may include a spectroscope which disperses the incident light into a spectrum in frequency band units, and a detection section which detects the intensity of the incident light dispersed into a spectrum.

(7) In the optical characteristic measuring apparatus of the invention, the optical system may include, instead of the light-receiving/spectroscopic means, spectroscopic means for subjecting the light including the predetermined band component to a spectroscopic process before the light is incident on the first polarizer, and light-receiving means for receiving the light which has been subjected to the spectroscopic process and has passed through the second polarizer; and in the spectrum extraction process, the spectral peaks may be extracted from a frequency spectrum obtained by analyzing a light intensity signal detected by the light-receiving means.

(8) In the optical characteristic measuring apparatus of the invention, the calculation means may calculate at least one of a principal axis direction of the measurement target and a retardation of the measurement target for the predetermined band component.

According to this configuration, since one or both of the principal axis direction and the retardation of the measurement target can be measured in one shot, the measurement can be extremely facilitated as compared with the related-art measuring apparatus and method.

(9) According to the invention, there is provided an optical characteristic measuring method according to the invention for measuring optical characteristics of a measurement target, the optical characteristic measuring method comprising:

a process of causing light including a predetermined band component to be incident on the measurement target through a first polarizer and a first carrier retarder and causing the light modulated by the measurement target to be incident on light-receiving/spectroscopic means through a second carrier retarder and a second polarizer, retardations of the first and second carrier retarders being known and differing from each other;

a spectrum extraction process of extracting a plurality of spectral peaks from a frequency spectrum obtained by analyzing a light intensity signal detected by the light-receiving/spectroscopic means; and a calculation process of performing an optical characteristic element calculation process of calculating an optical characteristic element representing the optical characteristics of the measurement target, based on the extracted spectral peaks and the retardations of the first and second carrier retarders.

(10) In the optical characteristic measuring method of the invention, at least one of a principal axis direction of the measurement target and a retardation of the measurement target for the predetermined band component may be calculated in the optical characteristic element calculation process.

BEST MODE FOR CARRYING OUT THE INVENTION

Preferred embodiments of the invention are described below with reference to the drawings.

(1) Configuration of Optical Characteristic Measuring Apparatus

Figure 1:
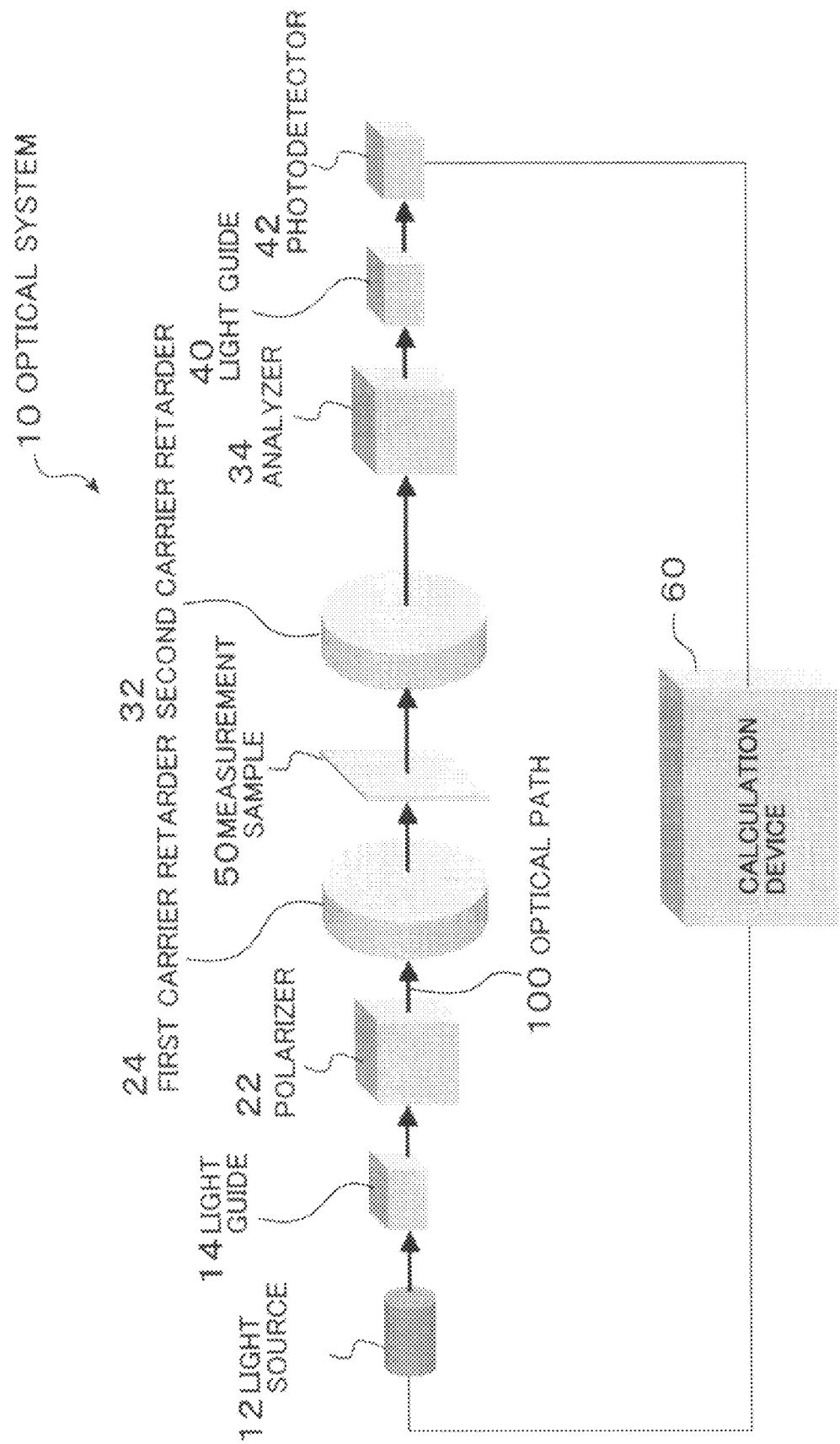
FIG. 1 is a diagram illustrative of a birefringence characteristic measuring apparatus according to one embodiment of the invention.

FIG. 1 shows an example of an optical characteristic measuring apparatus according to this embodiment. In this embodiment, the optical characteristic measuring apparatus is configured as a birefringence characteristic measuring apparatus. Note that the optical characteristic measuring apparatus according to the invention is not limited to the birefringence characteristic measuring apparatus.

The measuring apparatus according to this embodiment is configured as a device which optically measures the birefringence characteristics of a measurement sample 50 (measurement target) having optical transparency. In this embodiment, the measuring apparatus is configured to include an optical system 10 and a calculation device 60.

1-1 Optical System 10

The optical system 10 includes a light source 12 and a photodetector 42. The optical system 10 may further include a light guide 14, a polarizer 22, a first carrier retarder 24, the measurement sample 50 (measurement target), a second carrier retarder 32, an analyzer 34, and a light guide 40 disposed on an optical path 100 connecting the light source 12 and the photodetector 42. The analyzer 34 may be referred to as a polarizer which makes a pair with the polarizer 22. Specifically, the polarizer 22 may be referred to as a first polarizer, and the analyzer 34 may be referred to as a second polarizer. An optical system which does not include the light guides 14 and 40 may be used as the optical system 10.

The light source 12 is a device which generates and emits light including a predetermined wavelength (wave number k) band component. In this embodiment, a white light source such as a halogen lamp may be used as the light source 12.

The light guide 14 is an optical device which expands light from the light source 12 in the vertical and (or) horizontal directions corresponding to the measurement sample 50, and emits the resulting light. Specifically, the light guide 14 may be an optical device (optical element) for expanding a beam diameter, and may be referred to as a beam expander.

The polarizer 22 is an incident-side polarizer which makes a pair with the analyzer 34 and linearly polarizes the light emitted from the light guide 14.

The analyzer 34 is an exit-side polarizer which makes a pair with the polarizer 22 and linearly polarizes the light which has passed through the measurement sample 50.

The polarizer 22 and the analyzer 34 may be disposed so that an angle between the principal axis directions is an odd-numbered multiple of 45 degrees clockwise or counterclockwise. In this embodiment, the polarizer 22 and the analyzer 34 are disposed so that the principal axis direction of the analyzer 34 is in a position rotated clockwise by 45 degrees with respect to the principal axis direction of the polarizer 22.

The first carrier retarder 24 makes a pair with the second carrier retarder 32. The first and second carrier retarders 24 and 32 are respectively disposed on the optical path 100 on the upstream side and the downstream side of the measurement sample 50.

In this embodiment, the first and second carrier retarders 24 and 32 are used of which the retardations differ depending on the wavelength of light passing through the first and second carrier retarders 24 and 32. Therefore, the polarization state of light which has passed through the first and second carrier retarders 24 and 32 differs depending on the wavelength.

The first and second carrier retarders 24 and 32 may be formed by using high-order retardation plates, for example. The retardations of the first and second carrier retarders 24 and 32 are known and differ from each other. Specifically, when the retardation of the first carrier retarder 24 is $\alpha\delta$ and the retardation of the second carrier retarder 32 is $\beta\delta$, $\alpha$ and $\beta$ are set to be different values.

The first and second carrier retarders 24 and 32 are set so that the principal axis direction of the second carrier retarder 32 is in a position rotated clockwise or counterclockwise by an odd-numbered multiple of 45 degrees with respect to the principal axis direction of the first carrier retarder 24.

Moreover, the principal axis direction of the first carrier retarder 24 may be set to be in a position rotated clockwise or counterclockwise by an odd-numbered multiple of 45 degrees with respect to the principal axis direction of the polarizer 22. In this embodiment, the principal axis direction of the first carrier retarder 24 is in a position rotated by 45 degrees with respect to the principal axis direction of the polarizer 22.

Figure 2:
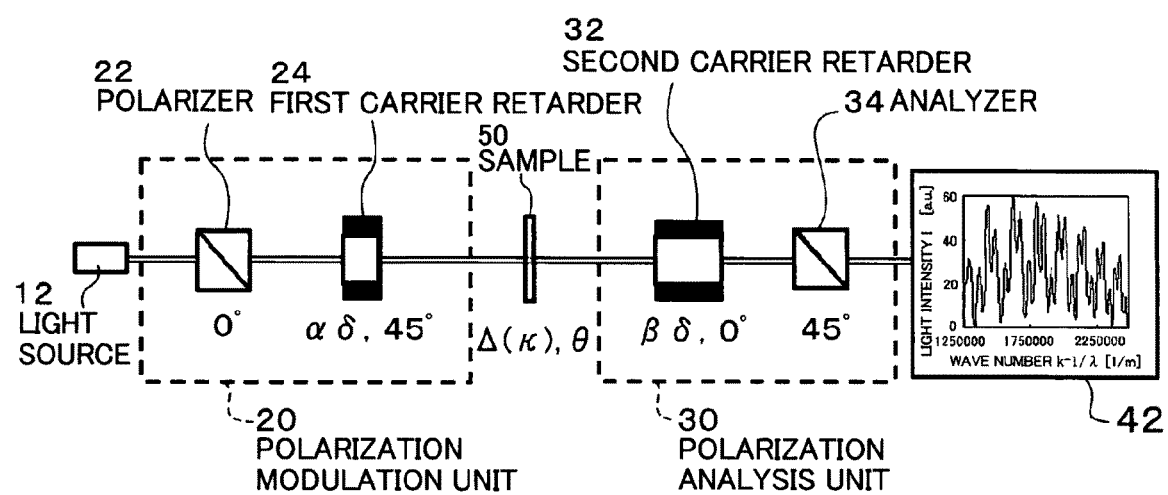
FIG. 2 is a diagram illustrative of the principle according to one embodiment of the invention.

FIG. 2 is a diagram showing the optical arrangement of the measurement sample 50, the polarizer 22, the first carrier retarder 24, the second carrier retarder 32, and the analyzer 34 on the optical path 100. Note that the light guides 14 and 40 are omitted for convenience of description.

In this embodiment, when the position of the principal axis direction of the polarizer 22 is 0 degree position, the principal axis directions of the first carrier retarder 24, the second carrier retarder 32, and the analyzer 34 are respectively in positions rotated clockwise by 45 degrees, 0 degree, and 45 degrees with respect to the principal axis direction of the polarizer 22, as shown in FIG. 2.

In this embodiment, the polarizer 22 and the first carrier retarder 24 positioned on the incident side of the measurement sample 50 may form a polarization modulation unit 20. The second carrier retarder 32 and the analyzer 34 positioned on the exit side of the measurement sample 50 may form a polarization analysis unit 30.

The measurement sample 50 is disposed on the optical path 100 between the first and second carrier retarders 24 and 32. The measurement sample 50 is a material (optical material) having optical transparency such as a liquid crystal or a functional optical film, for example.

1-2 Photodetector 42 as Light-Receiving/Spectroscopic Means

The photodetector 42 functions as a light-receiving/spectroscopic means, and includes a CCD 44 in which light-receiving sections 45 are two-dimensionally arranged.

Figure 3:
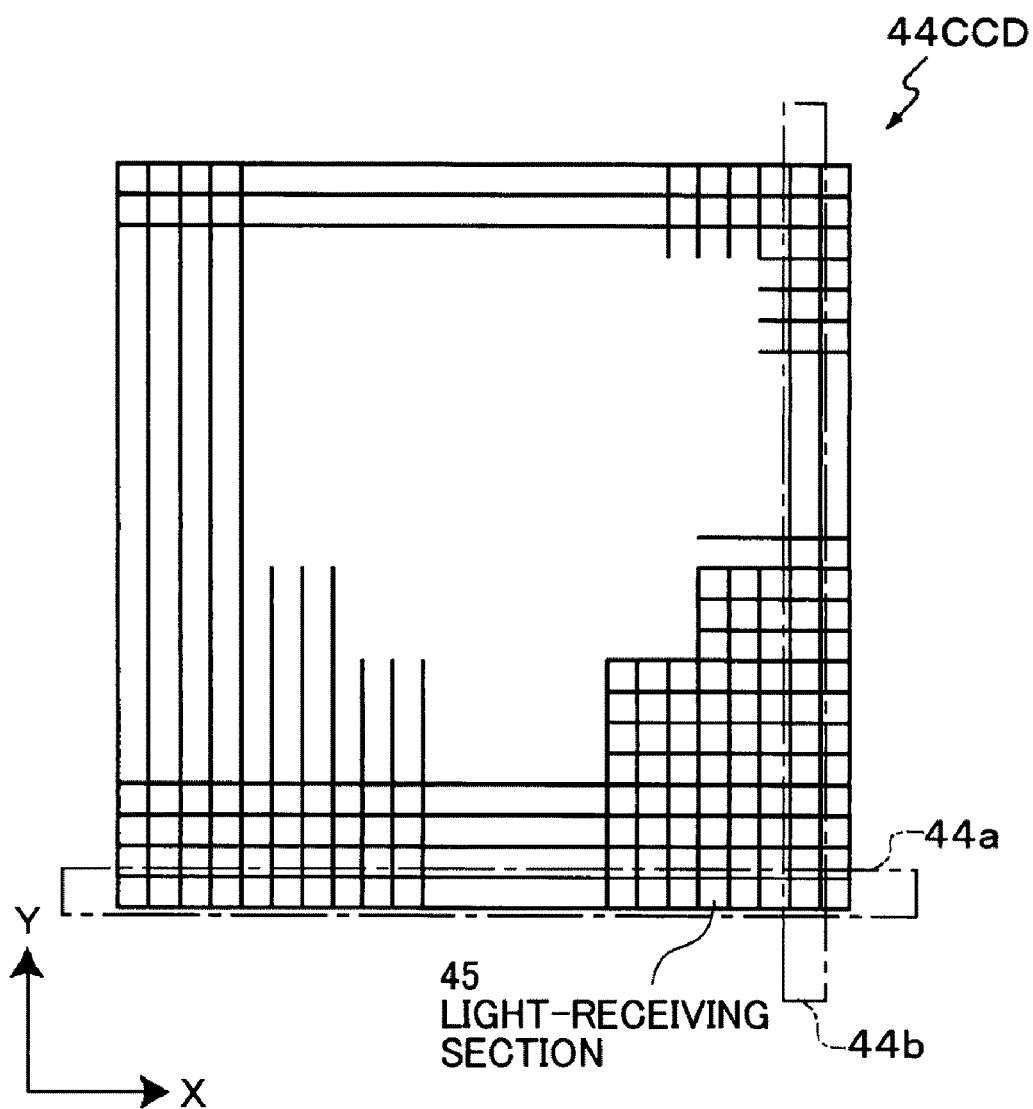
FIG. 3 is a diagram illustrative of a light-receiving surface of a CCD provided in a photodetector of an optical system shown in FIG. 1.

FIG. 3 is a diagram showing an example of the two-dimensional arrangement of the light-receiving sections 45 of the CCD 44 according to this embodiment. In the CCD 44 according to this embodiment, the light-receiving sections 45 are arranged in the X-axis direction and the Y-axis direction in a matrix. Each light-receiving section column 44a extending in the X-axis direction is associated with each position of the measurement sample 50 along the longitudinal direction. Each light-receiving section row 44b extending in the Y-axis direction is associated with each position of the measurement sample 50 along the lateral direction.

Light which has passed through the measurement sample 50 and then passed through the second carrier retarder 32 and the analyzer 34 is guided by the light guide 40 to be incident on each light-receiving section 45 of the CCD 44 corresponding to the longitudinal direction and the lateral direction of the measurement sample 50.

Figure 4:
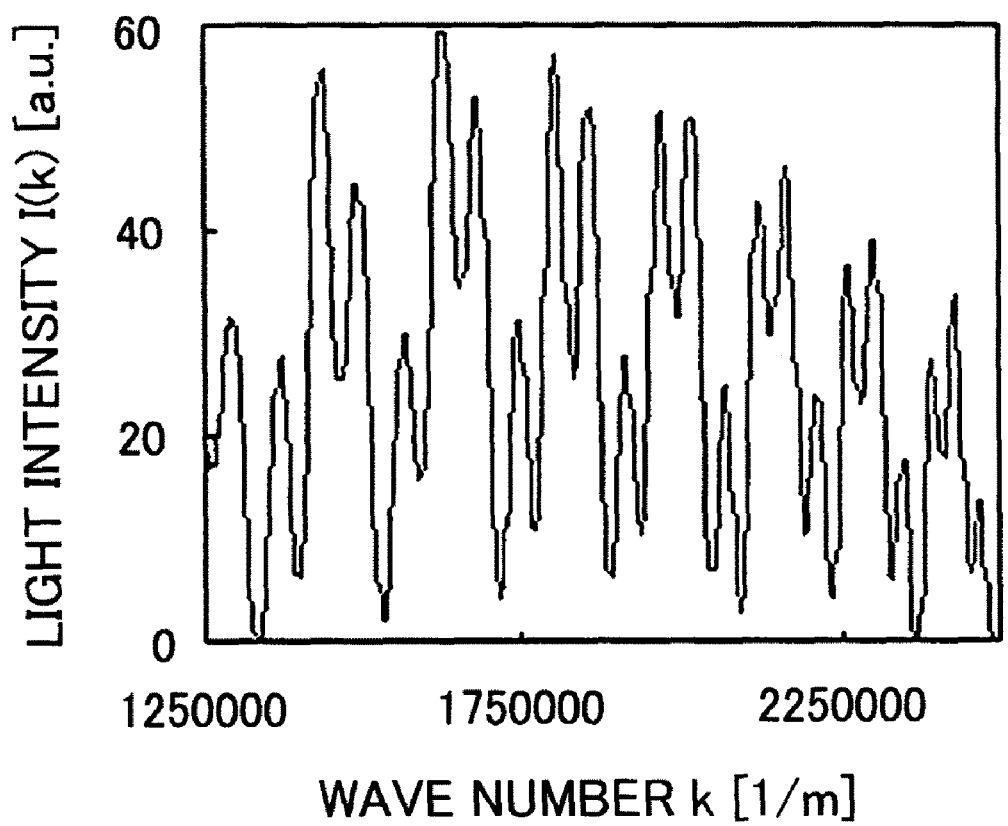
FIG. 4 shows an example of measurement data of a light intensity signal subjected to a spectroscopic process obtained by snap-shot measurement.

FIG. 4 shows an example of the light intensity I(k) detected by the light-receiving section 45 of the CCD 44 of the photodetector 42. Equations (7-1) and (7-2) described later are theoretical equations of the light intensity I(k). The light intensity I(k) obtained by the photodetector 42 is expressed as a function of the retardation $\Delta(k)$ and the principal axis direction $\theta$ of the measurement sample 50, as shown by the equations (7-1) and (7-2).

The calculation device 60 calculates the retardation $\Delta(k)$ for a predetermined band component at each position of the measurement sample 50 along the longitudinal direction and the lateral direction, and calculates the principal axis direction θ of the measurement sample 50 based on the light intensity signal I(k) detected by each light-receiving section 45 of the photodetector 42. The details are described later.

(2) Birefringence Characteristic Measurement Principle

The principle of the birefringence characteristic measuring apparatus (optical characteristic measuring apparatus in a broad sense) according to this embodiment is described below.

White light emitted from the light source 12 passes through the polarizer 22 and the first carrier retarder 24, as shown in FIGS. 1 and 2. The retardation of the first carrier retarder 24 differs depending on the wavelength of light which passes through the first carrier retarder 24, as described above. Therefore, the polarization state of light which has passed through the first carrier retarder 24 differs depending on the wavelength.

The light having a polarization state which differs depending on the wavelength (light which has passed through the first carrier retarder 24) passes through the measurement sample 50 having the retardation Δ(k) and the principal axis direction θ. The polarization state of the light is further modulated when the light passes through the measurement sample 50.

The light which has passed through the measurement sample 50 passes through the second carrier retarder 32 positioned on the downstream side of the measurement sample 50. The polarization state of the light is further modulated by the carrier retarder 32.

In this case, the retardations of the first and second retarders 24 and 32 are respectively referred to as αδ(k) and the βδ(k). k indicates the wave number, and α is not equal to β.

The principal axis directions of the polarizer 22, the first carrier retarder 24, the second carrier retarder 32, and the analyzer 34 are 0 degree, 45 degrees, 0 degree, and 45 degrees, respectively.

The light which has passed through the optical system 10 as described passes through the analyzer 34 and is incident on the photodetector 42 as measurement light which is frequency-modulated with respect to the wavelength.

In this embodiment, the light source 12 emits light (white light) including a predetermined band component. Therefore, light (measurement light) which has passed through the analyzer 34 and is incident on the light-receiving/spectroscopic means also includes the predetermined band component. The intensity of the measurement light in wave number k units shown in FIG. 4 can be measured by dispersing light incident on the light-receiving/spectroscopic means into a spectrum in wave number k units and measuring the light intensity (spectral intensity) in wave number k units. In order to implement the above configuration, the light-receiving/spectroscopic means may include a spectroscopic means (spectroscope) for dispersing the measurement light into a spectrum, and a light-receiving means (light-receiving element) for measuring the light intensity. The light-receiving/spectroscopic means may be configured to acquire the light intensity in wave number k units by measuring the intensity of light dispersed into a spectrum by the spectroscope (e.g. prism or grating) by using the light-receiving element. The light-receiving means may have a structure in which light-receiving elements which photoelectrically convert the incident light are disposed in parallel. The intensity of the measurement light in wave number units can be detected by assigning each light-receiving element to one of the wave numbers. In this case, the spectroscope and the light-receiving element may be collectively referred to as a light-receiving/spectroscopic device (light-receiving/spectroscopic means). The optical system may include a plurality of light-receiving/spectroscopic devices. The light intensity in a predetermined region of the measurement sample 50 can be acquired by associating each light-receiving/spectroscopic device with each position of the measurement sample 50. The light-receiving/spectroscopic devices may be two-dimensionally arranged. For example, the light-receiving/spectroscopic devices may be arranged in one row or column. Alternatively, the light-receiving/spectroscopic devices may be arranged in rows and columns.

2-1 Mueller Matrix of Optical System 10

The Mueller matrices of the optical system 10 can be expressed as follows.

$$P_0 = \frac{1}{2}\begin{bmatrix} 1 & 1 & 0 & 0 \\ 1 & 1 & 0 & 0 \\ 0 & 0 & 0 & 0 \\ 0 & 0 & 0 & 0 \end{bmatrix} \quad (1)$$

$$A_{45} = \frac{1}{2}\begin{bmatrix} 1 & 0 & 1 & 0 \\ 0 & 0 & 0 & 0 \\ 1 & 0 & 1 & 0 \\ 0 & 0 & 0 & 0 \end{bmatrix} \quad (2)$$

$$R_0 = \begin{bmatrix} 1 & 0 & 0 & 0 \\ 0 & 1 & 0 & 0 \\ 0 & 0 & \cos\alpha\delta(k) & \sin\alpha\delta(k) \\ 0 & 0 & -\sin\alpha\delta(k) & \cos\alpha\delta(k) \end{bmatrix} \quad (3)$$

$$R_{45} = \begin{bmatrix} 1 & 0 & 0 & 0 \\ 0 & \cos\beta\delta(k) & 0 & -\sin\beta\delta(k) \\ 0 & 0 & 0 & 0 \\ 0 & \sin\beta\delta(k) & 0 & \cos\beta\delta(k) \end{bmatrix} \quad (4)$$

-continued $$X_{\Delta,\phi} = \begin{bmatrix} 1 & 0 & 0 & 0 \\ 0 & 1-(1-\cos\Delta(k))\sin^2 2\theta & (1-\cos\Delta(k))\sin 2\theta\cos 2\theta & -\sin\Delta(k)\sin 2\theta \\ 0 & (1-\cos\Delta(k))\sin 2\theta\cos 2\theta & 1-(1-\cos\Delta(k))\cos^2 2\theta & \sin\Delta(k)\cos 2\theta \\ 0 & \sin\Delta(k)\sin 2\theta & -\sin\Delta(k)\cos 2\theta & \cos\Delta(k) \end{bmatrix} \quad (5)$$

$$= \begin{bmatrix} m_{00} & m_{01} & m_{02} & m_{03} \\ m_{10} & m_{11} & m_{12} & m_{13} \\ m_{20} & m_{21} & m_{22} & m_{23} \\ m_{30} & m_{31} & m_{32} & m_{33} \end{bmatrix}$$

The relationship between each Mueller matrix and the Stokes parameters can be expressed as follows.

$$S_{out} = A_{45} \cdot R_0 \cdot X_{\Delta,\phi} \cdot R_{45} \cdot P_0 \cdot S_{in} \quad (6)$$

$S_{out} = \{s_0, s_1, s_2, s_3\}^T = \{I_H + I_V, I_H - I_V, I_{+45^\circ} - I_{-45^\circ}, I_R - I_L\}^T$ and $S_{in} = \{1, 0, 0, 0\}$ respectively indicate the output Stokes parameter and the input Stokes parameter. $I_H$, $I_V$, $I_{+45^\circ}$, $L_{-45^\circ}$, $I_R$, and $I_L$ respectively indicate the light intensities of linearly polarized components oriented at 0 degree and 90 degrees, the light intensities of linearly polarized components oriented at ±45 degrees, and the light intensities of clockwise and counterclockwise circularly polarized components. When substituting the equations (1) to (5), $S_{out}$, and $S_{in}$ in the equation (6), the light intensity I(k) can be expressed as follows.

$$I(k) = \frac{1}{8}(2m_{00} + (m_{21}(k) + m_{33}(k))\cos(\alpha - \beta)\delta(k) + \quad (7\text{-}1)$$
$$(m_{21}(k) - m_{33}(k))\cos(\alpha + \beta)\delta(k) + (-m_{23}(k) + m_{31}(k))$$
$$\sin(\alpha - \beta)\delta(k) + (m_{23}(k) + m_{31}(k))\sin(\alpha + \beta)\delta(k))$$

The coefficients $m_{21}(k)$, $m_{23}(k)$, $m_{31}(k)$, and $m_{33}(k)$ in the equation (7-1) contain information relating to the retardation $\Delta(k)$ of the measurement sample 50 for a predetermined wavelength band (wave number k) and information relating to the principal axis direction $\theta$ of the measurement sample 50, as shown by the following equation.

$$m_{21}(k) = \sin^2\frac{\Delta(k)}{2}\sin 4\theta, \quad (7\text{-}2)$$
$$m_{23}(k) = \sin\Delta(k)\cos 2\theta,$$
$$m_{31}(k) = \sin\Delta(k)\sin 2\theta,$$
$$m_{33}(k) = \cos\Delta(k)$$

k indicates the wave number which is the reciprocal of the wavelength $\lambda$. If $a_0 = 2m_{00}/8$, $a_{\alpha-\beta}(k) = (m_{21}(k) + m_{33}(k))/8$, $a_{\alpha+\beta}(k) = (m_{21}(k) - m_{33}(k))/8$, $b_{\alpha-\beta}(k) = (-m_{23}(k) + m_{31}(k))/8$, $b_{\alpha+\beta}(k) = (m_{23}(k) + m_{31}(k))/8$ \quad (8)

then the light intensity can be rewritten as follows.

$I(k) = a_0 + a_{\alpha-\beta}(k)\cos(\alpha-\beta)\delta(k) + a_{\alpha+\beta}(k)\cos(\alpha+\beta)\delta(k) + b_{\alpha-\beta}(k)\sin(\alpha-\beta)\delta(k) + b_{\alpha+\beta}(k)\sin(\alpha+\beta)\delta(k)$ \quad (9)

Transforming the equation yields the following equation.

$$I(k) = a_0 + \sqrt{a_{\alpha-\beta}(k)^2 + b_{\alpha-\beta}(k)^2}\cos\left(\begin{array}{c}(\alpha-\beta)\delta(k) - \\ \tan^{-1}\frac{b_{\alpha-\beta}(k)}{a_{\alpha-\beta}(k)}\end{array}\right) + \quad (10)$$
$$\sqrt{a_{\alpha+\beta}(k)^2 + b_{\alpha+\beta}(k)^2}\cos\left(\begin{array}{c}(\alpha+\beta)\delta(k) - \\ \tan^{-1}\frac{b_{\alpha+\beta}(k)}{a_{\alpha+\beta}(k)}\end{array}\right)$$

This equation is substituted as follows.

$I(k) = \text{bias} + \text{amp}_{\alpha-\beta}(k)\cdot\cos((\alpha-\beta)\delta(k) - \phi_{\alpha-\beta}(k)) + \text{amp}_{\alpha+\beta}(k)\cdot\cos((\alpha+\beta)\delta(k) - \phi_{\alpha+\beta}(k))$ \quad (11)

This equation indicates that the light intensity is modulated by the frequencies $(\alpha-\beta)\delta(k)$ and $(\alpha+\beta)\delta(k)$.

FIG. 4 shows an example of the intensity of light received by the light-receiving section 45 of the photodetector 42 in the optical system 10. In FIG. 4, the vertical axis indicates the light intensity I(k), and the horizontal axis indicates the wave number k. As shown in FIG. 4, it is confirmed that the intensity of light detected by the photodetector 42 is modulated by different frequencies.

Therefore, the wavelength dependence $\Delta(k)$ of the retardation and the principal axis direction $\theta$ can be separately measured by detecting the amplitude component and the phase component (analyzing the light intensity signal in a broad sense) by using a Fourier transform method.

Solving the equation (11) by using Euler's formula yields the following equation $$I(k) = \text{bias} + c_{\alpha-\beta}(k) + c^*_{\alpha-\beta}(k) + c_{\alpha+\beta}(k) + c^*_{\alpha+\beta}(k) \quad (12)$$

where, $$c_{\alpha-\beta}(k) = \frac{1}{2}\text{amp}_{\alpha-\beta}(k)\cdot\exp(i((\alpha-\beta)\delta(k) - \phi_{\alpha-\beta}(k))) \quad (13)$$
$$c_{\alpha+\beta}(k) = \frac{1}{2}\text{amp}_{\alpha+\beta}(k)\cdot\exp(i((\alpha+\beta)\delta(k) - \phi_{\alpha+\beta}(k)))$$

and $c_{\alpha-\beta}^*(k)$ and $c_{\alpha+\beta}^*(k)$ respectively indicate conjugate components of $c_{\alpha-\beta}(k)$ and $c_{\alpha+\beta}(k)$.

Inverse Fourier transformation of the equation (12) with respect to the wave number k yields the following equation.

$F^{-1}[I(k)] = \tilde{I}(\nu) = \text{Bias} + C_{\alpha-\beta}(\nu) + C_{\alpha-\beta}^*(\nu) + C_{\alpha+\beta}(\nu) + C_{\alpha+\beta}^*(\nu)$ \quad (14)

Figure 5:
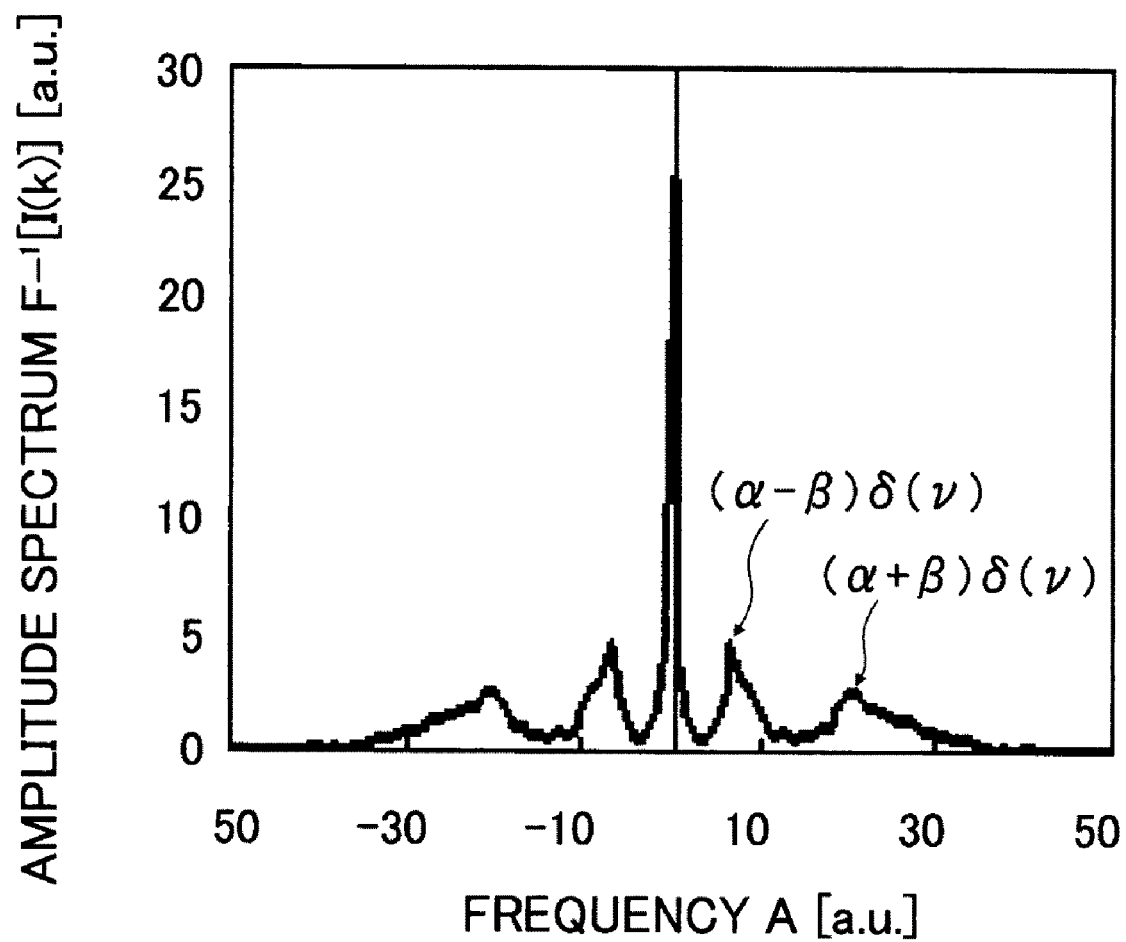
FIG. 5 is a graph showing a Fourier spectrum obtained from the light intensity signal shown in FIG. 4.

FIG. 5 shows the Fourier spectrum (frequency spectrum in a broad sense) shown by the equation (14). In FIG. 5, the horizontal axis indicates the frequency A, and the vertical axis indicates the amplitude spectrum.

As shown in FIG. 5, in the Fourier spectrum obtained by subjecting the light intensity I(k) modulated by the first and second carrier retarders 24 and 32 with the frequencies $(\alpha-\beta)\delta(k)$ and $(\alpha+\beta)\delta(k)$ of the retardations to inverse Fourier transformation with respect to the wave number k, a bias spectral peak appears in the region in which the frequency A is 0, and two spectral peaks respectively appear at the frequencies $(\alpha-\beta)\delta(\nu)$ and $(\alpha+\beta)\delta(\nu)$.

2-2 Utilization of Measured Values

In this embodiment, the light intensity signal I(k) detected by the light-receiving section 45 of the photodetector 42 and subjected to the spectroscopic process is used for calculations as described below.

Specifically, the light intensity signal I(k) subjected to the spectroscopic process as shown in FIG. 4 and shown by the equation (12) is subjected to inverse Fourier transformation with respect to the wave number k to determine a Fourier spectrum. The above-mentioned two spectral peaks $C_{\alpha-\beta}(\nu)$ and $C_{\alpha+\beta}(\nu)$ are extracted from the Fourier spectrum by filtering and subjected to Fourier transformation to determine the values of the following equation as measured values.

$$F[C_{\alpha-\beta}(\nu)] = c_{\alpha-\beta}(k)$$

$$F[C_{\alpha+\beta}(\nu)] = c_{\alpha+\beta}(k) \tag{15-1}$$

Specifically, the values of the equation (15-1) can be determined as the measured values from the light intensity signal I(k) detected by the photodetector 42 (light-receiving/spectroscopic means).

2-3 Calculation of Retardation $\Delta(k)$ and Principal Axis Direction $\theta$ of Measurement Sample 50 by Using Measured Values The equation (15-1) is expressed by the following equation utilizing the equation (13).

$$F[C_{\alpha-\beta}(\nu)] = c_{\alpha-\beta}(k) \tag{15-2}$$

$$= \frac{1}{2} amp_{\alpha-\beta}(k) \cdot \exp\left(i\begin{pmatrix}(\alpha-\beta)\delta(k) - \\ \phi_{\alpha-\beta}(k)\end{pmatrix}\right)$$

$$F[C_{\alpha+\beta}(\nu)] = c_{\alpha+\beta}(k)$$

$$= \frac{1}{2} amp_{\alpha+\beta}(k) \cdot \exp\left(i\begin{pmatrix}(\alpha+\beta)\delta(k) - \\ \phi_{\alpha+\beta}(k)\end{pmatrix}\right)$$

From the equation (15-2), $amp_{\alpha-\beta}$, $\phi_{\alpha-\beta}$, $amp_{\alpha+\beta}$, and $\phi_{\alpha+\beta}$ can be expressed as follows based on the real number component Re and the imaginary number component Im of each spectral peak and the retardations $\alpha\delta(k)$ and $\beta\delta(k)$ of the first and second carrier retarders 24 and 32.

$$amp_{\alpha-\beta}(k) = \sqrt{\text{Re}[c_{\alpha-\beta}(k)]^2 + \text{Im}[c_{\alpha-\beta}(k)]^2}, \tag{16}$$

$$(\alpha-\beta)\delta(k) - \phi_{\alpha-\beta}(k) = \tan^{-1}\frac{\text{Im}[c_{\alpha-\beta}(k)]}{\text{Re}[c_{\alpha-\beta}(k)]}$$

$$amp_{\alpha+\beta}(k) = \sqrt{\text{Re}[c_{\alpha+\beta}(k)]^2 + \text{Im}[c_{\alpha+\beta}(k)]^2},$$

$$(\alpha+\beta)\delta(k) - \phi_{\alpha+\beta}(k) = \tan^{-1}\frac{\text{Im}[c_{\alpha+\beta}(k)]}{\text{Re}[c_{\alpha+\beta}(k)]}$$

From the equations (10) and (11), $a_{\alpha-\beta}(k)$, $a_{\alpha+\beta}(k)$, $b_{\alpha-\beta}(k)$, and $b_{\alpha+\beta}(k)$ can be expressed as follows by using $amp_{\alpha-\beta}(k)$, $\phi_{\alpha-\beta}(k)$, $amp_{\alpha+\beta}(k)$, and $\phi_{\alpha+\beta}(k)$.

$$a_{\alpha-\beta}(k) = amp_{\alpha-\beta}(k) \cdot \cos\phi_{\alpha-\beta}(k), \; a_{\alpha+\beta}(k) = amp_{\alpha+\beta}(k) \cdot \cos\phi_{\alpha+\beta}(k),$$

$$b_{\alpha-\beta}(k) = amp_{\alpha-\beta}(k) \cdot \sin\phi_{\alpha-\beta}(k), \; b_{\alpha+\beta}(k) = amp_{\alpha+\beta}(k) \cdot \sin\phi_{\alpha+\beta}(k) \tag{17}$$

Since the retardations $\alpha\delta(k)$ and $\beta\delta(k)$ of the first and second carrier retarders 24 and 32 of the optical system 10 are known, the values $a_{\alpha-\beta}(k)$, $a_{\alpha+\beta}(k)$, $b_{\alpha-\beta}(k)$, and $b_{\alpha+\beta}(k)$ can be obtained from the equations (16) and (17).

Since the retardation $\Delta(k)$ and the principal axis direction $\theta$ can be expressed as follows from the equations (5) and (8)

$$\Delta(k) = \tan^{-1}\frac{\sqrt{m_{23}(k)^2 + m_{31}(k)^2}}{m_{33}(k)} \tag{18}$$

$$= \tan^{-1}\frac{\sqrt{\left(\frac{b_{\alpha+\beta}(k) -}{b_{\alpha-\beta}(k)}\right)^2 + \left(\frac{b_{\alpha-\beta}(k) +}{b_{\alpha+\beta}(k)}\right)^2}}{a_{\alpha-\beta}(k) - a_{\alpha+\beta}(k)}$$

$$\theta = \frac{1}{2}\tan^{-1}\frac{m_{31}(k)}{m_{23}(k)}$$

$$= \frac{1}{2}\tan^{-1}\frac{b_{\alpha-\beta}(k) + b_{\alpha+\beta}(k)}{b_{\alpha+\beta}(k) - b_{\alpha-\beta}(k)},$$

the wavelength characteristics $\Delta(k)$ of the retardation and the principal axis direction $\theta$ can be calculated.

In this embodiment, the above series of measurement processes can be performed in units of the light-receiving sections 45 (in units of the light-receiving/spectroscopic devices) of the photodetector 42 which functions as the light-receiving/spectroscopic means.

In this embodiment, light emitted from the light source 12 passes through predetermined regions (e.g. entire surface) of the measurement sample 50, and is detected by the CCD 44 of the photodetector 42 in which the light-receiving sections 45 are arranged in the X and Y directions in a matrix, as shown in FIG. 3.

Therefore, snap-shot measurement can be achieved in which the wavelength characteristics $\Delta(k)$ of the retardation in predetermined regions of the measurement sample 50 and the principal axis direction $\theta$ of the measurement sample 50 can be determined at the same time by applying the measurement light only once from the light source 12.

In this embodiment, when the retardations of the first and second carrier retarders 24 and 32 are $\alpha\delta$ and $\beta\delta$, the retardations of the first and second carrier retarders 24 and 32 may be set so that the ratio of $(\alpha+\beta)$ to $(\alpha-\beta)$ is two or more or ½ or less. This enables the difference in frequency between the two spectral peaks to be sufficiently increased in the Fourier spectrum shown in FIG. 5. This makes it possible to more accurately measure the birefringence characteristics of the measurement sample 50.

(3) Measurement of Birefringence Characteristics

Figure 6:
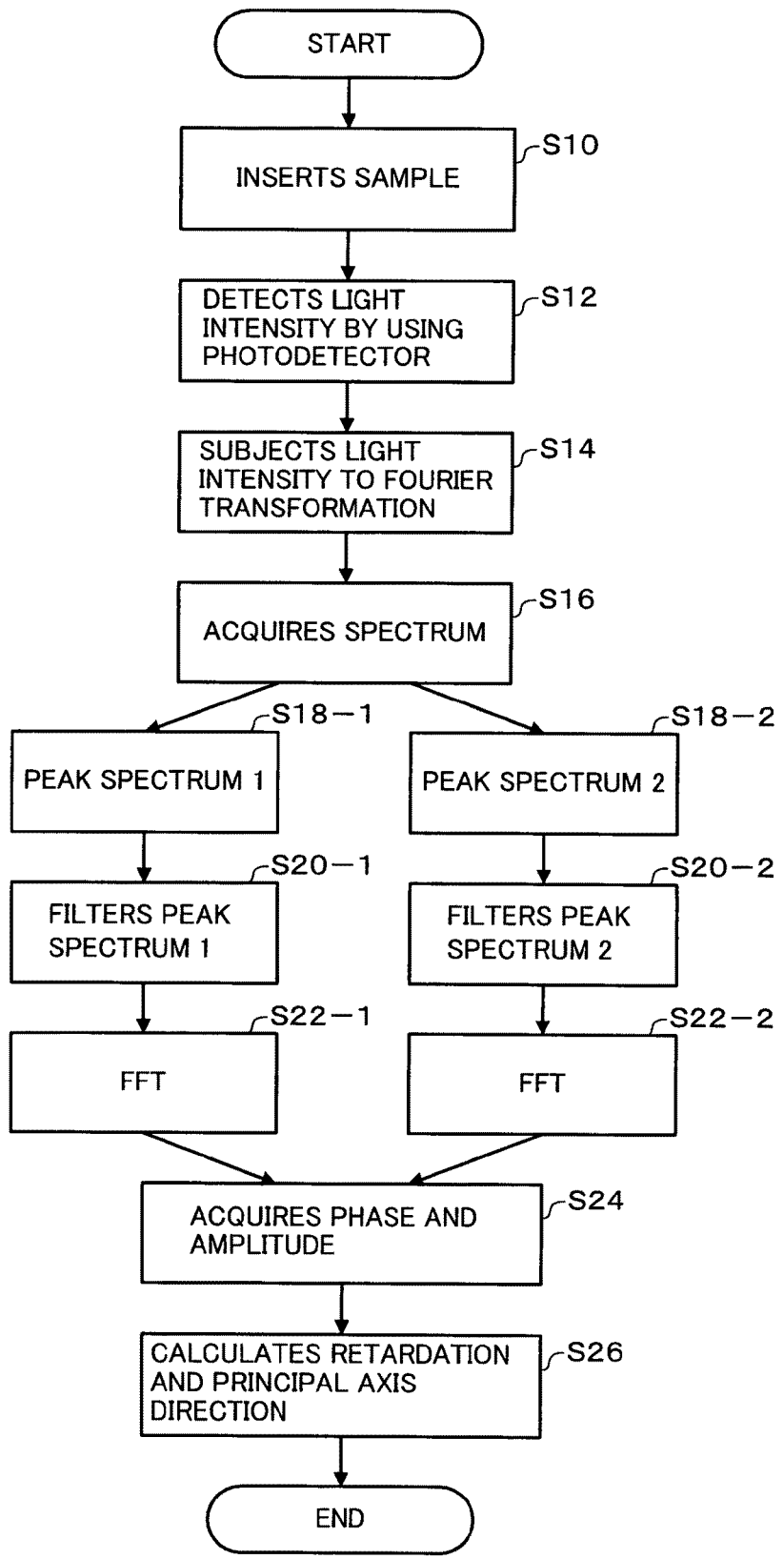
FIG. 6 is a flowchart showing the operation of a device according to one embodiment of the invention.

FIG. 6 is a flowchart of the operation of the measuring apparatus according to this embodiment, particularly showing a flowchart of the calculation procedure of the calculation device 60.

When measuring the birefringence characteristics, the measurement sample 50 is inserted into the optical path 100 of the optical system 10 (step S10).

Light is emitted from the light source 12 and caused to pass through the measurement sample 50. The light which has passed through the measurement sample 50 is received by the photodetector 42 to detect the light intensity (step S12). In this case, the photodetector 42 functions as the light-receiving/spectroscopic means. Light received by each light-receiving section 45 arranged in a matrix, as shown in FIG. 3, may be detected as the light intensity signal I(k) shown in FIG. 4 in units of the light-receiving sections. In this case, light received by the light-receiving sections 45 is subjected to the spectroscopic process in units of the light-receiving sections, and detected as the light intensity signal I(k), as shown in FIG. 4.

The light intensity signal is then subjected to Fourier transformation (inverse Fourier transformation) with respect to the wave number k as shown by the equation (14) (step S14) to obtain a Fourier spectrum (step S16). As shown in FIG. 5, the Fourier spectrum thus obtained contains two spectral peaks $C_{\alpha-\beta}(\nu)$ and $C_{\alpha+\beta}(\nu)$ reflecting the retardations $\alpha\delta(k)$ and $\beta\delta(k)$ specific to the first and second carrier retarders 24 and 32.

In the subsequent steps S18-1, S18-2, S20-1, and S20-2, the spectral peaks $C_{\alpha-\beta}(\nu)$ and $C_{\alpha+\beta}(\nu)$ are extracted from the Fourier spectrum by filtering.

In the subsequent steps S22-1 and S22-2, the spectral peaks $C_{\alpha-\beta}(\nu)$ and $C_{\alpha+\beta}(\nu)$ thus extracted are subjected to Fourier transformation based the equation (15-1).

As described above, the two spectral peaks are extracted as measured values in the steps S12 to S22 from the light intensity signal of the measurement light obtained by each light-receiving section 45. These processes may be generically referred to as a spectrum extraction process. Alternatively, the steps S12 to S20 may be referred to as a spectrum extraction process, and the step S22 may be referred to as an analysis process after the spectrum extraction process.

In this embodiment, a birefringence characteristic calculation process for calculating the birefringence characteristics of the measurement sample 50 is performed in steps S24 and S26.

Specifically, the equation (15-2) is derived from the spectral peaks shown by the equation (15-1) and the equation (13), and a series of calculations shown by the equations (16) to (18) is performed (steps S24 and S26).

This allows the wavelength characteristics $\Delta(k)$ of the retardation and the principal axis direction $\theta$ (optical characteristic elements in a broad sense) of the measurement sample 50 to be calculated in units of the light-receiving sections 45 (in units of the light-receiving/spectroscopic means).

In the CCD 44 shown in FIG. 3, each light-receiving section 45 arranged in the X and Y directions in a matrix corresponds to each region of the measurement sample 50. Therefore, whether or not a predetermined region of the measurement sample 50 has appropriate characteristics can be determined by measuring the birefringence characteristics in units of the light-receiving sections 45. When a defective portion exists in the measurement sample 50, the position of the defective portion can be accurately specified in addition to the presence or absence of the defective portion.

(4) Other Embodiments

The above embodiment has been described taking an example in which the retardations of the first and second carrier retarders 24 and 32 of the optical system 10 are known in advance. Note that the invention is not limited thereto. The invention may also be implemented even if the retardations of the first and second carrier retarders 24 and 32 are unknown. Specifically, the retardations of the carrier retarders 24 and 32 can be determined by using the measuring apparatus according to this embodiment. The measurement target can be measured by using the determined retardations as the known values.

Figure 7:
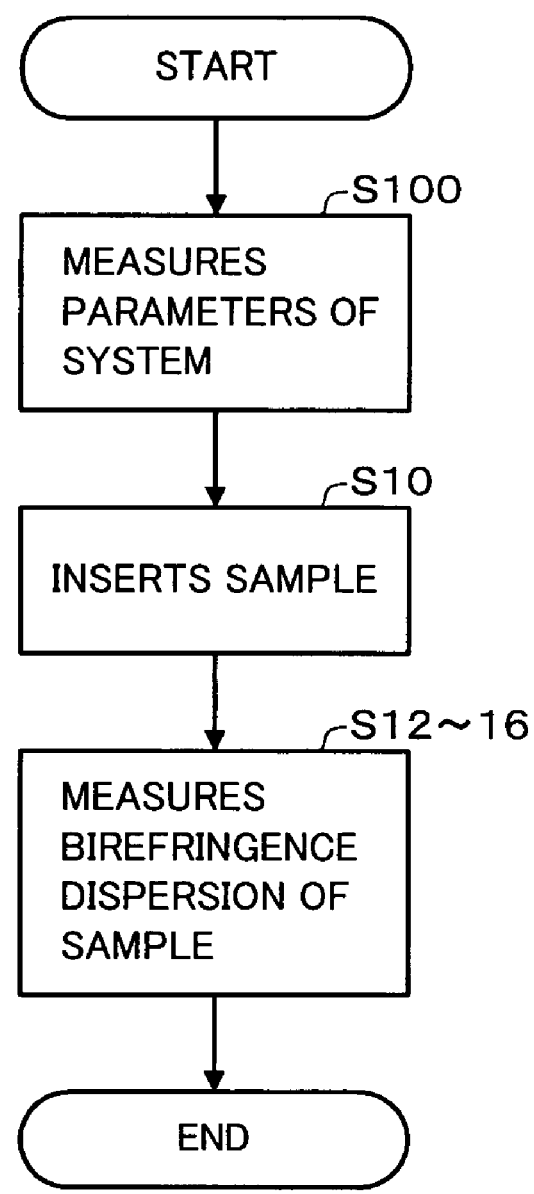
FIG. 7 is a flowchart showing a process when measuring parameters of first and second carrier retarders in advance and then measuring a measurement sample.

FIG. 7 shows a flowchart of the process according to this embodiment.

The parameters of the first and second carrier retarders 24 and 32 are measured in a step S100.

In this case, the measurement sample 50 is not inserted into the optical system 10 shown in FIG. 1, and a snap-shot measurement is performed in the same manner as in the above embodiment in a state in which the measurement sample 50 is not provided.

In this case, the values relating to the measurement sample 50 (i.e., $\phi_{\alpha-\beta}(k)$ and $\phi_{\alpha+\beta}(k)$) do not exist in the equation (15-2).

Therefore, the wavelength characteristics $\alpha\delta(k)$ and $\beta\delta(k)$ of the retardations of the first and second carrier retarders 24 and 32 can be determined based on the equation (16).

The wavelength characteristics $\alpha\delta(k)$ and $\beta\delta(k)$ of the retardations thus determined are stored in a storage means of the calculation device 60 as the known values, whereby the birefringence characteristics of the measurement sample 50, that is, the wavelength characteristics of the retardation and the principal axis direction can be determined in the steps S10 and S12 to S26 in the same manner as in the above embodiment.

(5) Verification Experiment

A simulation was carried out as a verification experiment.

The first and second carrier retarders 24 and 32 were formed by bonding 1–λ wave films generally used for a liquid crystal display taking the birefringence dispersion characteristics into consideration. The first carrier retarder 24 was formed by bonding twenty wave films as a retarder having a retardation of 20λ at a wavelength of 550 nm. The second carrier retarder 32 was formed by bonding forty wave films as a retarder having a retardation of 40λ at a wavelength of 550 nm.

As the measurement sample 50, a sample was used of which the principal axis direction and the retardation were known in advance. In this simulation, a quarter-wave film used for a liquid crystal display was used.

The light intensity signal I(k) subjected to the spectroscopic process shown in FIG. 4 was obtained by this simulation. When observing the light intensity I(k) from the resulting data, it was confirmed that a plurality of frequencies occurred.

FIG. 5 shows a Fourier spectrum obtained by subjecting the light intensity signal shown in FIG. 4 to Fourier analysis. In this Fourier spectrum, two spectral peaks respectively occur at two positions specified by the retardations of the first and second carrier retarders set as the simulation conditions.

Figure 8:
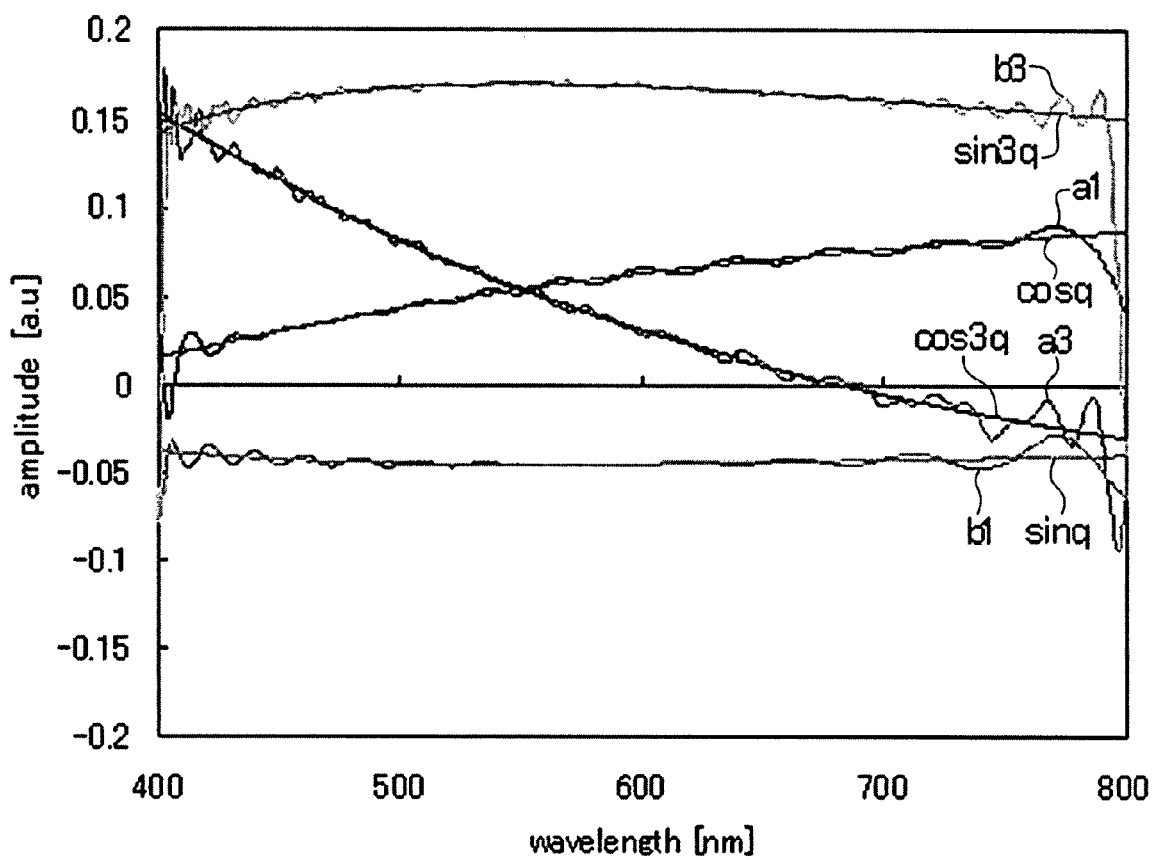
FIG. 8 is a graph showing a comparison between an amplitude component of each frequency obtained by a simulation and an amplitude component of the frequency of the set light intensity.

FIG. 8 shows simulation data of the value of each component in the equation (17). The simulation data indicates that the amplitude component of each frequency coincides with the amplitude component of the frequency of the set light intensity. Specifically, the simulation results a1, a3, b1, and b3 respectively coincide with the theoretical values cos q, cos 3q, sin q, and sin 3q.

Figure 9:
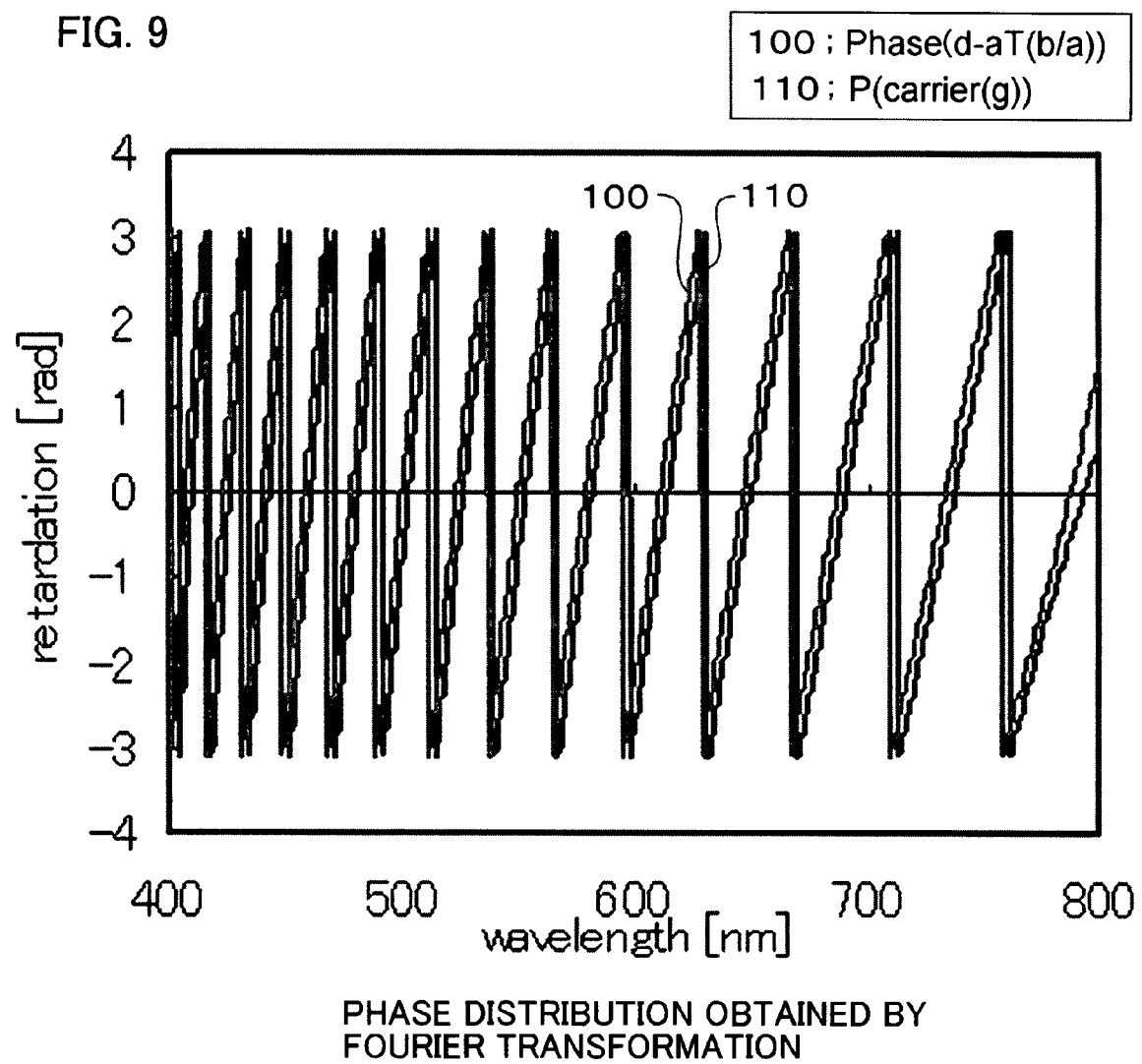
FIG. 9 is a graph showing a change in phase of measurement light before and after inserting a measurement sample into an optical system.

FIG. 9 shows the phase of light received by the photodetector 42. In FIG. 9, a reference numeral 100 indicates the phase of light in a state in which the measurement sample 50 is inserted into the optical system 10, and a reference numeral 110 indicates the phase of light in a state in which the measurement sample 50 is not inserted into the optical system 10. It was confirmed that the phase changes to only a small extent when the measurement sample 50 is inserted.

Figure 10:
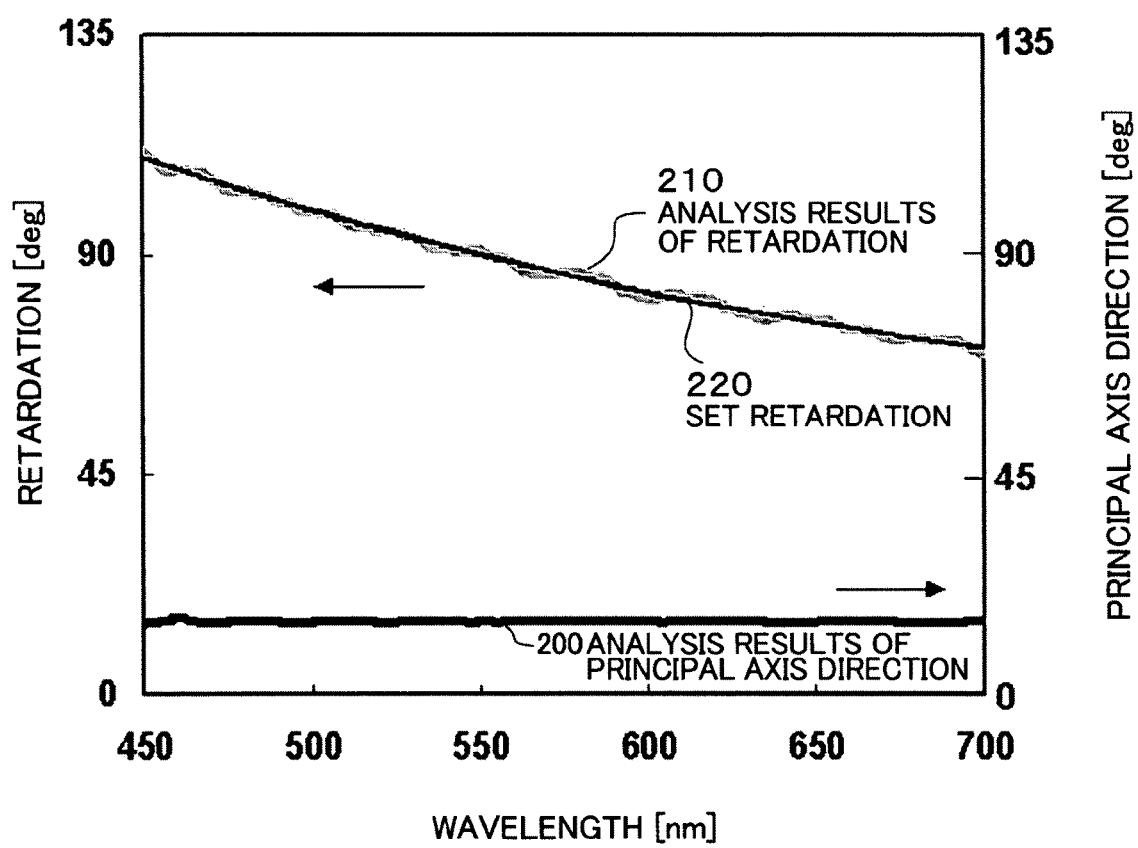
FIG. 10 is a graph showing simulation analysis results of the principal axis direction and the retardation of a measurement sample.

FIG. 10 shows the wavelength dependence of the retardation and the principal axis direction of the measurement sample 50 determined from the phase and the amplitude shown in FIGS. 8 and 9. In FIG. 10, reference numerals 200 and 210 indicate the analysis results of the principal axis direction and the retardation obtained by the simulation, and a reference numeral 220 indicates the known retardation of the measurement sample 50. The principal axis direction of the measurement sample 50 was set at 15 degrees. As shown in FIG. 10, the value obtained by the simulation closely coincides with the actual value of the measurement sample 50.

Figure 11:
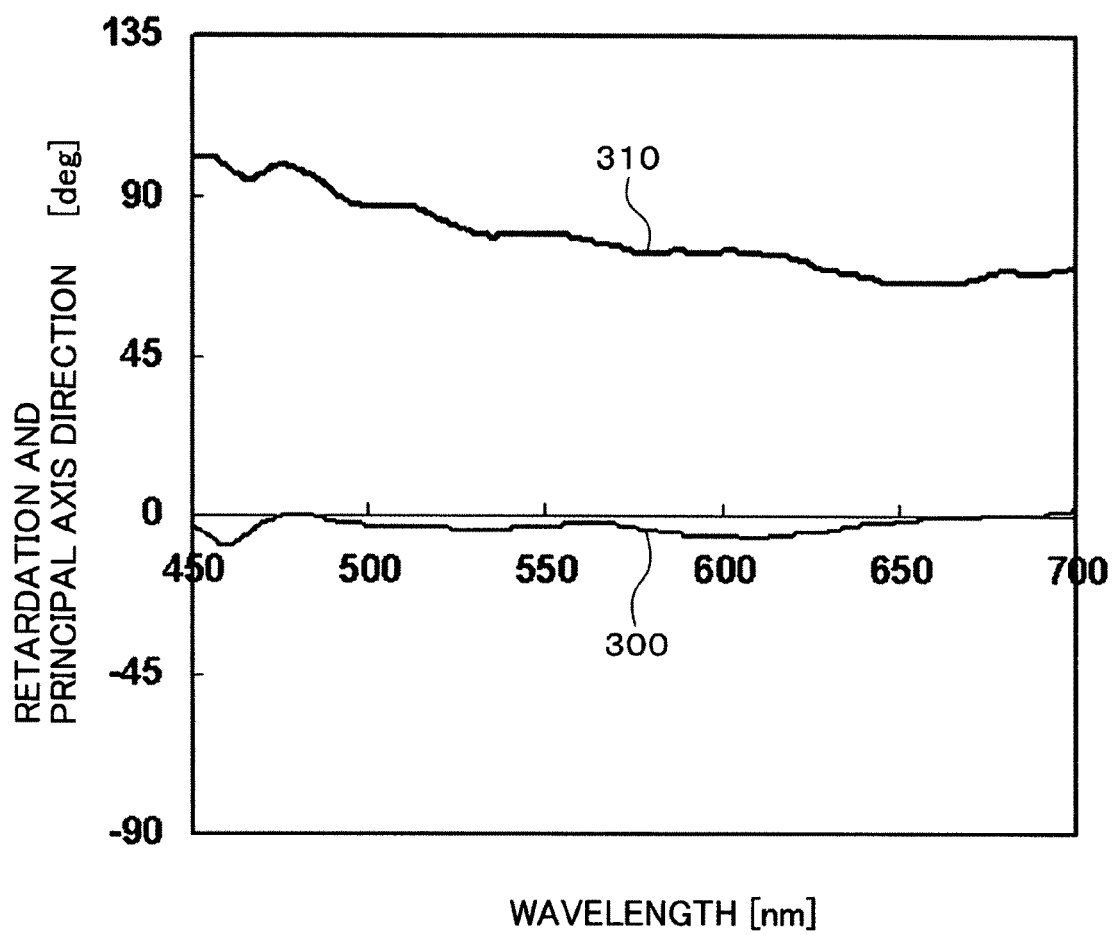
FIG. 11 is a graph showing actual experimental data of the birefringence dispersion characteristics and the principal axis direction obtained by using an actual measurement sample.

FIG. 11 shows the actual experimental results.

As the measurement sample 50, a retardation plate was used which produces a retardation of 72.9 degrees at a wavelength of 633 nm. The measurement sample was set so that the principal axis direction was 0 degree.

In FIG. 11, solid lines 300 and 310 respectively indicate the principal axis direction and the retardation of the measurement sample 50 obtained by the experiment. As shown in FIG. 11, the retardation is 72 degrees at a wavelength of 623 nm. Therefore, the effectiveness of the measuring method according to this embodiment was confirmed. The principal axis direction was 0 degree over the entire wavelength range. This also confirms the effectiveness of the measuring method according to this embodiment.

As described above, the measuring apparatus according to this embodiment can simultaneously measure the retardation and the principal axis direction of the measurement sample 50 by snap-shot measurement without requiring mechanical and electrical operations. Therefore, the measuring method according to this embodiment can be applied to a wide variety of fields such as a liquid crystal display as a polymer material evaluation method.

For example, a liquid crystal display currently used may include a material having birefringence such as a retardation film or a liquid crystal. The measuring method according to this embodiment is effective for evaluating such a material. A next-generation mobile liquid crystal display increasingly utilizes a polymer film instead of a glass substrate. The measuring method according to this embodiment also contributes to development of such an advanced material technology. The measuring method according to this embodiment can be applied not only to the polymer material field, but also to biotechnology and medical fields.

The invention is not limited to the above embodiments. Various modifications and variations are possible without departing the spirit and scope of the invention.

For example, the above embodiments have been described taking an example in which the principal axis direction and the retardation of the measurement sample 50 are measured in one shot. Note that the invention is not limited thereto. If necessary, only one of the principal axis direction and the retardation may be measured.

The invention is not limited to the above embodiments. Various modifications and variations may be made. For example, the invention includes configurations substantially the same as the configurations described in the embodiments (in function, in method and effect, or in objective and effect). The invention also includes configurations in which an unsubstantial portion described in the embodiments is replaced. The invention also includes configurations having the same effects as the configurations described in the embodiments, or configurations capable of achieving the same objective as the configurations described in the embodiments. Further, the invention includes configurations in which a known technique is added to the configurations described in the embodiments.

For example, the measuring apparatus has been described in the above embodiments which is configured to cause light (e.g. white light) including a band component to be incident on the optical element and dispersed into a spectrum and acquire the intensity of the measurement light in wave number k units. Note that the invention may be applied to any method capable of acquiring the intensity of the measurement light in wave number k units (see FIG. 4). In other words, the invention may be applied to any method capable of acquiring the modulated state of light in wave number k (wavelength) units as light intensity. For example, a configuration may be employed in which the intensity of a predetermined band component of measurement light is acquired without dispersing the measurement light into a spectrum by continuously emitting light (monochromatic light) at a specific wave number (wavelength) while changing the wave number (wavelength). In this case, the measuring apparatus may include a spectroscopic means which disperses white light into a spectrum between the light source 12 and the polarizer 22. Alternatively, any light source capable of continuously emitting light with a different wavelength (wave number) may be used as the light source. In this case, a prompt measurement can also be achieved since it is unnecessary to change the setting of the principal axis direction of the optical element.

The measuring apparatus has been described in the above embodiments which measures the optical characteristics (principal axis direction and retardation) of a measurement target having optical transparency. Note that the invention can also be applied to a measurement target which does not have optical transparency. Specifically, the invention can also be applied to a measurement target which reflects light. In this case, the optical system may be configured so that light emitted from the light source 12 is caused to be incident on the measurement sample 50 through the polarizer 22 and the first carrier retarder 24, and the light reflected by the measurement sample 50 is caused to be incident on the light-receiving/spectroscopic means through the second carrier retarder 32 and the analyzer 34.

The measuring apparatus has been described in the above embodiments which measures the principal axis direction and the retardation as the optical characteristics. Note that the invention is not limited thereto. Specifically, the optical characteristic measuring apparatus according to the embodiments of the invention may be configured as a measuring apparatus which calculates matrix elements of a matrix (e.g. Mueller matrix) representing optical characteristics. Alternatively, the optical characteristic measuring apparatus according to the embodiments of the invention may be configured as a measuring apparatus which measures the dichroism of the measurement sample 50.

INDUSTRIAL APPLICABILITY

The invention can be utilized for evaluation of organic polymer materials such as a liquid crystal and research and development of new materials. The invention can also be applied to quality control of a polymer orientation state. A finding obtained therefrom is very effective for new materials.

Moreover, it becomes possible to inspect inorganic materials such as semiconductors and optical crystals and measure the photoelastic constant and the stress distribution occurring in the materials. It is also possible to determine the state of stress applied to optical elements by real-time monitoring using the invention. Since the invention enables snap-shot measurement, the birefringence dispersion characteristics of a fast phenomenon can be detected.

The invention can also be applied to the field of biotechnology in addition to the above organic and inorganic polymer materials.

The invention claimed is:

1. An optical characteristic measuring apparatus for measuring optical characteristics of a measurement target, the optical characteristic measuring apparatus comprising:
   an optical system including first and second carrier retarders formed by irrotational high-order retardation plates and having retardations being known and differing from each other, the optical system causing light including a predetermined band component to be incident on the measurement target through a first polarizer and the first carrier retarder and causing the light modulated by the measurement target to be incident on light-receiving/spectroscopic means through the second carrier retarder and a second polarizer; and
   calculation means for performing a spectrum extraction process of extracting a plurality of spectral peaks from a frequency spectrum obtained by analyzing a light intensity signal detected by the light-receiving/spectroscopic means, and an optical characteristic element calculation process of calculating an optical characteristic element representing the optical characteristics of the measurement target based on the spectral peaks and the retardations of the first and second carrier retarders.

2. The optical characteristic measuring apparatus as defined in claim 1, wherein the calculation means performs the spectrum extraction process before the optical characteristic element calculation process in a state in which the measurement target is not provided in the optical system, and calculates the retardations of the first and second carrier retarders as the known values based on the extracted spectral peaks.

3. The optical characteristic measuring apparatus as defined in claim 1, wherein the optical system is set so that:
   a principal axis direction of the second polarizer is in a position rotated clockwise or counterclockwise by an odd-numbered multiple of 45 degrees with respect to a principal axis direction of the first polarizer;
   a principal axis direction of the second carrier retarder is in a position rotated clockwise or counterclockwise by an odd-numbered multiple of 45 degrees with respect to a principal axis direction of the first carrier retarder; and
   the principal axis direction of the first carrier retarder is in a position rotated clockwise or counterclockwise by an odd-numbered multiple of 45 degrees with respect to the principal axis direction of the first polarizer.

4. The optical characteristic measuring apparatus as defined in claim 1, wherein the calculation means calculates real number components and imaginary number components of the spectral peaks extracted by the spectrum extraction process, and performs the optical characteristic element calculation process based on the real number components and the imaginary number components of the spectral peaks and the retardations of the first and second carrier retarders.

5. The optical characteristic measuring apparatus as defined in claim 1, wherein, when the retardations of the first and second carrier retarders are $\alpha\Delta$ and $\beta\Delta$ the retardations of the first and second carrier retarders are set so that a ratio of $(\alpha+\beta)$ to $(\alpha-\beta)$ is two or more, or ½ or less.

6. The optical characteristic measuring apparatus as defined in claim 1,
   wherein the light-receiving/spectroscopic means includes a plurality of light-receiving sections arranged two-dimensionally;
   wherein the optical system is configured so that the light including the predetermined band component is incident on a predetermined region of the measurement target and the light modulated by the measurement target is incident on the light-receiving sections; and
   wherein the calculation means performs the spectrum extraction process and the optical characteristic element calculation process in units of the light-receiving sections to calculate the optical characteristic element in the predetermined region of the measurement target.

7. The optical characteristic measuring apparatus as defined in claim 1,
   wherein the optical system includes, instead of the light-receiving/spectroscopic means, spectroscopic means for subjecting the light including the predetermined band component to a spectroscopic process before the light is incident on the first polarizer, and light-receiving means for receiving the light which has been subjected to the spectroscopic process and has passed through the second polarizer; and
   wherein, in the spectrum extraction process, the spectral peaks are extracted from a frequency spectrum obtained by analyzing a light intensity signal detected by the light-receiving means.

8. The optical characteristic measuring apparatus as defined in claim 1, wherein the calculation means calculates at least one of a principal axis direction of the measurement target and a retardation of the measurement target for the predetermined band component.

9. An optical characteristic measuring method for measuring optical characteristics of a measurement target, the optical characteristic measuring method comprising:
   a process of using first and second carrier retarders formed by irrotational high-order retardation plates causing light including a predetermined band component to be incident on the measurement target through a first polarizer and a first carrier retarder and causing the light modulated by the measurement target to be incident on light-receiving/spectroscopic means through a second carrier retarder and a second polarizes, retardations of the first and second carrier retarders being known and differing from each other;
   a spectrum extraction process of extracting a plurality of spectral peaks from a frequency spectrum obtained by analyzing a light intensity signal detected by the light-receiving/spectroscopic means; and
   a calculation process of performing an optical characteristic element calculation process of calculating an optical characteristic element representing the optical characteristics of the measurement target, based on the extracted spectral peaks and the retardations of the first and second carrier retarders.

10. The optical characteristic measuring method as defined in claim 9, wherein at least one of a principal axis direction of the measurement target and a retardation of the measurement target for the predetermined band component is calculated in the optical characteristic element calculation process.

* * * * *